(12) United States Patent
Nakano

(10) Patent No.: US 9,008,496 B2
(45) Date of Patent: Apr. 14, 2015

(54) PROBE

(71) Applicant: Shimadzu Corporation, Kyoto-shi, Kyoto (JP)

(72) Inventor: Tomohito Nakano, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 152 days.

(21) Appl. No.: 13/788,393

(22) Filed: Mar. 7, 2013

(65) Prior Publication Data

US 2013/0243412 A1     Sep. 19, 2013

(30) Foreign Application Priority Data

Mar. 14, 2012  (JP) .................................. 2012-056576

(51) Int. Cl.
- *F24H 1/10* (2006.01)
- *F24H 3/00* (2006.01)
- *G01N 30/72* (2006.01)

(52) U.S. Cl.
CPC ............ *F24H 3/002* (2013.01); *G01N 30/7246* (2013.01); *G01N 30/7253* (2013.01); *G01N 30/7266* (2013.01)

(58) Field of Classification Search
None
See application file for complete search history.

(56) References Cited

U.S. PATENT DOCUMENTS

| | | | |
|---|---|---|---|
| 6,794,646 B2* | 9/2004 | Tong et al. ..................... 250/288 |
| 8,076,639 B2* | 12/2011 | Cooks et al. .................. 250/288 |
| 2002/0145845 A1* | 10/2002 | Hunt et al. ..................... 361/303 |
| 2003/0003595 A1* | 1/2003 | Amirav ........................... 436/173 |
| 2003/0189170 A1* | 10/2003 | Covey et al. ................... 250/288 |
| 2004/0094706 A1* | 5/2004 | Covey et al. ................... 250/288 |
| 2006/0054805 A1* | 3/2006 | Flanagan et al. .............. 250/288 |
| 2010/0171033 A1* | 7/2010 | Jolliffe et al. ................. 250/282 |
| 2010/0275780 A1* | 11/2010 | Bailey et al. .................... 95/285 |
| 2010/0303917 A1* | 12/2010 | Watson et al. ................. 424/489 |
| 2011/0042567 A1* | 2/2011 | Yamaguchi .................... 250/288 |
| 2011/0303839 A1* | 12/2011 | Robb ............................. 250/282 |
| 2012/0017899 A1* | 1/2012 | Yeates ....................... 128/203.12 |
| 2013/0039838 A1* | 2/2013 | Lashmore et al. ........... 423/447.1 |
| 2013/0248615 A1* | 9/2013 | Yeates ................................ 239/9 |

FOREIGN PATENT DOCUMENTS

JP          2001-343363 A      12/2001

* cited by examiner

*Primary Examiner* — Thor Campbell
(74) *Attorney, Agent, or Firm* — Sughrue Mion, PLLC

(57) ABSTRACT

A probe including a liquid sample channel through which a liquid sample flows in a specified direction; a nebulizer gas channel through which a nebulizer gas flows in a specified direction, formed at the outer circumference of the liquid sample channel so as to have a round annular outer circumference and be coaxial with the liquid sample channel; a heating gas channel for injecting an assist gas in a specified direction, wherein a heating gas injection port is formed around the outlet end of the nebulizer gas channel so as to have a round annular outer circumference and be coaxial with the nebulizer gas channel; and a heating element which is arranged inside the heating gas channel and heats the assist gas for injecting through the heating gas injection port.

4 Claims, 4 Drawing Sheets

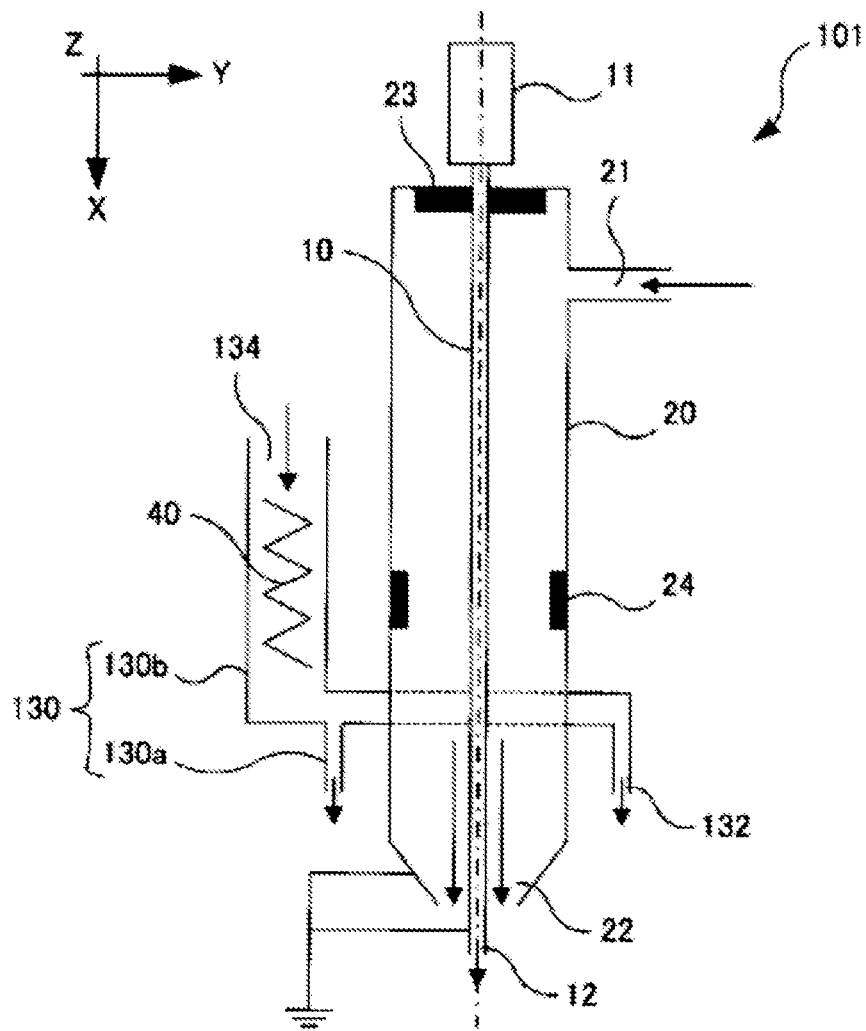

PROBE

This application claims priority from Japanese Patent Application No. 2012-056576, filed Mar. 14, 2012, the entire contents of which are herein incorporated by reference.

TECHNICAL FIELD

The present invention relates to a probe, more specifically, to an ESI probe which ionizes a liquid sample eluted from a liquid chromatography unit.

BACKGROUND ART

A liquid chromatography/mass spectrometry device (LC/MS) comprises a liquid chromatography unit (LC unit) which separates and elutes a liquid sample into individual components, an ionization chamber which ionizes the eluted sample components coming from the LC unit, and a mass spectrometry unit (MS unit) which detects ions introduced from the ionization chamber. Various types of ionization means may be used in this sort of ionization chamber for ionizing the liquid sample, but electrospray ionization (ESI), atmospheric pressure chemical ionization (APCI) and other atmospheric pressure ionization methods are widely used.

Specifically, for APCI, the tip of a nozzle connected to the end of the column of the LC unit is disposed toward the inside of the ionization chamber, and a needle electrode is arranged in front of the nozzle tip. Drops of the sample which has been atomized by heating in the nozzle are ionized by chemically reacting with carrier gas ions (buffer ions) generated by corona discharge from the needle electrode. Furthermore, for ESI, the tip of the nozzle connected to the end of the column of the LC unit is disposed toward the inside of the ionization chamber, and a high voltage on the order of several kV is applied to the tip of the nozzle to generate a strong non-uniform electric field. As a result, the liquid sample undergoes charge separation due to the electric field and is pulled apart and atomized by coulombic attraction. As a result, the solvent in the drop comes into contact with the surrounding air and evaporates, and gas ions are generated.

FIG. 3 is a simplified diagram illustrating an example of a liquid chromatography/mass spectrometry device using ESI. It will be noted that a direction perpendicular to the ground is taken as the X direction (specified direction), the direction parallel to the ground and perpendicular to the X direction is taken as the Y direction, and the direction perpendicular to the X direction and Y direction is taken as the Z direction.

In the liquid chromatography/mass spectrometry device, an ionization chamber 211, a first intermediate chamber 212 adjacent to the ionization chamber 211, a second intermediate chamber 213 adjacent to the first intermediate chamber 212, and a mass spectrometry chamber (MS unit) 214 adjacent to the second intermediate chamber 213 are disposed contiguously across intervening partition walls (for example, see Patent Literature 1). In this sort of liquid chromatography/mass spectrometry device, the liquid sample separated into components in the LC unit 11 is supplied to the ESI probe 101 via liquid sample channel 10. Furthermore, a nebulizer gas (for example, nitrogen gas) is supplied to the ESI probe 101 via nebulizer gas inlet channel 25. Furthermore, an assist gas (for example, nitrogen gas) is supplied to the ESI probe 101 via assist gas inlet channel 35. As a result, the liquid sample is nebulized inside the ionization chamber 211 by the ESI probe 101.

Here, FIG. 4 is a cross-sectional view of the ESI probe shown in FIG. 3. ESI probe 101 comprises a round tubular liquid sample channel 10 through which the liquid sample flows in the X direction, a round annular nebulizer gas channel 20 through which nebulizer gas flows in the X direction, a round annular heating gas channel 130 through which assist gas flows in the X direction, and a heater 40 arranged in the heating gas channel 130.

The liquid sample channel 10 is of a thin round tubular shape made of metal, the top end of which is connected to LC connection part 11, and a liquid sample channel outlet 12 is formed at its bottom end. Thus, the liquid sample introduced through the LC connection part 11 flows through the inside of the liquid sample channel 10 in the X direction and is then injected in the X direction through the liquid sample channel outlet 12.

The nebulizer gas channel 20 is of a fat round tubular shape made of metal, being formed around the outer circumference of the liquid sample channel 10, with a round annular outer circumference and coaxial with the liquid sample channel 10, wherein a nebulizer gas inlet 21 is formed at the top end and a nebulizer gas outlet 22 is formed on the bottom end around the liquid sample channel outlet 12 so as to have a round annular outer circumference and be coaxial with the liquid sample channel 10. Based on this sort of nebulizer gas channel 20, the nebulizer gas introduced through the nebulizer gas inlet 21 flows in the X direction between the outside of the liquid sample channel 10 and the inside of the nebulizer gas channel 20, and is then injected in the X direction through the nebulizer gas outlet 22. Thus, the liquid sample which has been injected through the liquid sample channel outlet 12 takes on the form of a mist due to the effect of collision with the nebulizer gas injected through the area around the liquid sample channel outlet 12, and is nebulized inside the ionization chamber 211.

Furthermore, wires are connected to apply a high voltage of several kV from a voltage source (not illustrated) to the bottom end of the liquid sample channel 10 and the bottom end of the nebulizer gas channel 20, in order to carry out ionization of the liquid sample. It will be noted that, since a high voltage is to be applied to the bottom end of the liquid sample channel 10 and the bottom end of the nebulizer gas channel 20, a resin component or rubber component (electrical insulator) 23 of round annular outer circumference coaxial with the liquid sample channel 10 is arranged between the top end of the nebulizer gas channel 20 and the liquid sample channel 10, and a resin component or rubber component (electrical insulator) 24 of round annular outer circumference coaxial with the liquid sample channel 10 is arranged in the middle of the nebulizer gas channel 20.

The heating gas channel 130 comprises a round annular channel 130a formed around the bottom end of the nebulizer gas channel 20 so as to have a round annular outer circumference and be coaxial with the nebulizer gas channel 20; and a round tubular heating channel 130b which is connected to a portion of the top end of the round annular channel 130a. A heating gas inlet 134 is formed at the top end of the heating channel 130b, a heater 40 is arranged inside in the center of the heating channel 130b, and the bottom end of the heating channel 130b is connected to a portion of the top end of the round annular channel 130a. Furthermore, a heating gas outlet nozzle 132, with an annual outer circumference and coaxial with the nebulizer gas channel 20, is formed at the bottom end of the round annular channel 130a around the nebulizer gas outlet 22. It will be noted that a space creating a predetermined minimum distance (for example, 20 mm) is provided between the outside of the nebulizer gas channel 20 and the inside of the heating gas channel 130 so as to prevent the transfer of heat of the heater 40 and of heat of the heated nebulizer gas.

Based on a heating gas channel 130 of this sort, assist gas introduced through the heating gas inlet 134 is heated to around 500° C. by the heater 40 as it passes through the heating channel 130b in the X direction, and flows through the round annular channel 130a in the X direction and is then injected in the X direction through the heating gas outlet nozzle 132. As a result, the organic solvent of liquid samples containing organic solvent is gasified by the assist gas, increasing the liquid sample ionization efficiency. Furthermore, the spreading of the nebulized sample is constrained by the flow of assist gas, increasing the ionized sample density in the MS unit 214 and contributing to increased sensitivity.

Ions generated in the ionization chamber 211 by this sort of ESI probe 101, passing sequentially through a desolvating tube 219, then a first ion lens 221 and skimmer 222 inside the first intermediate chamber 212, then an octapole 223 and focus lens 224 inside the second intermediate chamber 213, and then inlet lens 225, are fed into the MS unit 214, unwanted ions are removed by quadrupoles 216 and 217, and only specified ions which reach the detector 218 are detected.

PRIOR ART LITERATURES (Patent literature 1) Japanese Unexamined Patent Application Publication 2001-343363

SUMMARY OF THE INVENTION

Now, in an ESI probe 101 of this sort, if the heat of the heater 40 and the heat of the heating gas which has been heated to about 500° C. transfers to the metal liquid sample channel 10, the temperature of the liquid sample flowing through the liquid sample channel 10 will reach boiling point and boil, and the sample may undergo thermal decomposition or the resin components or rubber components (electrical insulators) 23 and 24 may deform due to heat.

Furthermore, the bottom end of the liquid sample channel 10 can be displaced substantially in parallel in relation to the nebulizer gas channel 20 within a predetermined range of the YZ plane orthogonal to the X axis by means of a position adjustment knob (not illustrated), allowing the position to be adjusted as appropriate, or allowing retraction and extension in the X axis direction in relation to the nebulizer gas channel 20 (allowing the amount of protrusion to be adjusted), making it possible to adjust the position as appropriate.

Thus, it is necessary to prevent the heat of the heater 40 and the heat of the assist gas from being transferred to the metal liquid sample channel 10, so that the sample will not undergo thermal decomposition and so that the electrical insulators 23 and 24 will not be degraded by heat, and also so as to allow the user to adjust the position of the liquid sample channel 10 without sustaining burns. To this end, a space is provided to create a predetermined minimum distance (for example 20 mm) between the outside of the nebulizer gas channel 20 and the inside of the heating gas channel 130, but in this case, there is the problem that the ESI probe 101 becomes larger. It will be noted that the placement of thermal insulating material between the outside of the nebulizer gas channel 20 and the inside of the heating gas channel 130 may also be considered, but this has the problem of leading to an increase in cost.

Thus, it is the object of the present invention to provide a probe that can be reduced in size.

The probe of the present invention, made to resolve the aforementioned problem, is a probe comprising: a tubular liquid sample channel through which a liquid sample flows in a specified direction; a nebulizer gas channel through which a nebulizer gas flows in the specified direction, formed at the outer circumference of said liquid sample channel so as to have a round annular outer circumference and be coaxial with the liquid sample channel; a heating gas channel for injecting an assist gas in the specified direction, wherein a heating gas injection port is formed around the outlet end of said nebulizer gas channel so as to have a round annular outer circumference and be coaxial with the nebulizer gas channel; and a heating element which is arranged inside said heating gas channel and heats the assist gas for injecting through said heating gas injection port, said probe further comprising an assist gas channel formed in all or part of the space between said nebulizer gas channel and heating gas channel, wherein the assist gas, prior to being heated by said heating element, flows through the assist gas channel, and the assist gas after being heated by said heating element flows through the heating gas channel.

Here, "specified direction" refers to any one direction determined in advance by the designer, etc., for example, the downward direction or the like.

With the probe of the present invention, an assist gas channel, through which (ambient temperature) assist gas flows before being heated, is formed between the nebulizer gas channel and the heating gas channel, so the heat of the heating element and the heat of the heated assist gas are not transferred to the liquid sample channel, and furthermore, the nebulizer gas channel can be cooled by the ambient temperature assist gas. As a result, the thermal insulation effect is increased, the need to provide a space so as to create a predetermined minimum distance between the outside of the nebulizer gas channel and the inside of the heating gas channel is eliminated, and the size of the probe can be reduced. Furthermore, it is possible to use electrical insulators of relatively low heat resistance, allowing costs to be reduced. Moreover, in cases where a thermal insulation material is used, the thermal insulation performance required of the thermal insulation material can be reduced.

Furthermore, the probe of the present invention can be made such that said assist gas channel is formed at the outer circumference of said nebulizer gas channel so as to have a round annular outer circumference and be coaxial with the nebulizer channel, wherein the assist gas prior to being heated by said heating element flows in a direction opposite to the specified direction, or in the specified direction.

Moreover, the probe of the present invention can be made such that said liquid sample channel is fabricated from metal, and a high voltage is applied to the outlet end of said liquid sample channel.

BRIEF DESCRIPTION OF THE DRAWINGS

FIG. 4 is a cross-sectional view of the ESI probe shown in FIG. 3.

DETAILED DESCRIPTION OF THE EXEMPLARY EMBODIMENTS

A mode of embodiment of the present invention will be described below using the drawings. It should be noted that the present invention is not limited to the mode of embodiment described below, and includes various modes so long as they do not depart from the gist of the present invention.

Figure 1:
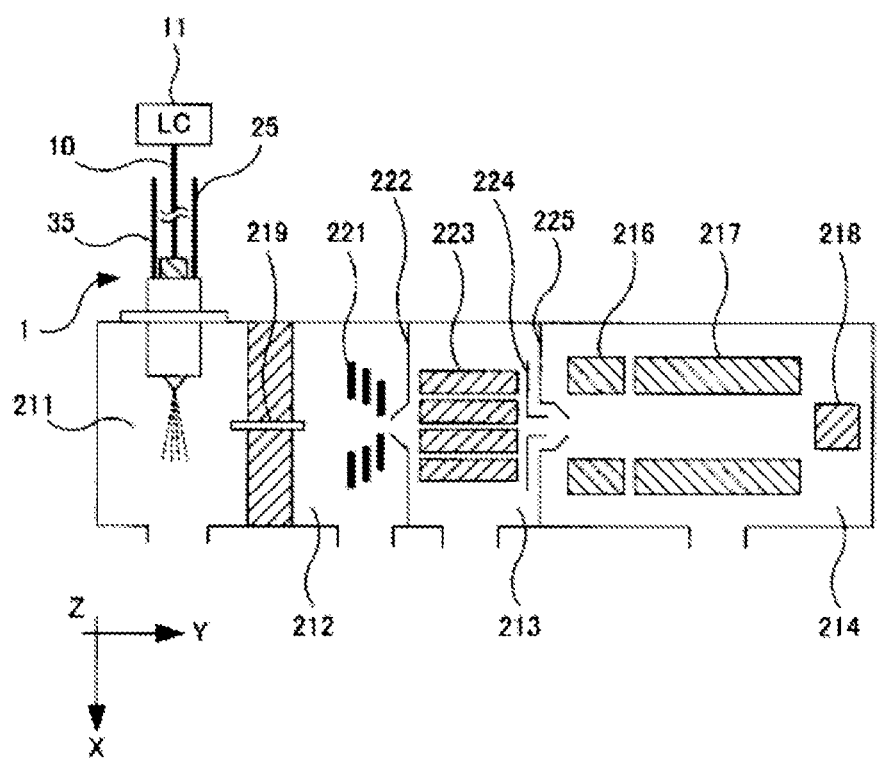
FIG. 1 is a simplified diagram illustrating an example of a liquid chromatography/mass spectrometry device using ESI according to the present invention.
Figure 2:
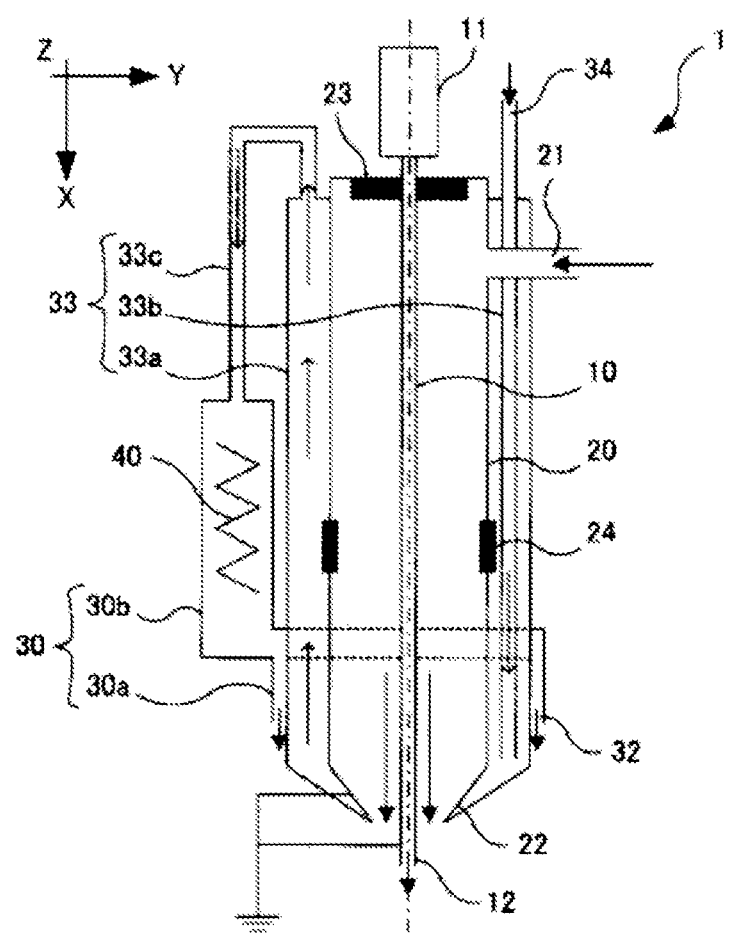
FIG. 2 is a cross-sectional view of the ESI probe shown in FIG. 1.
Figure 3:
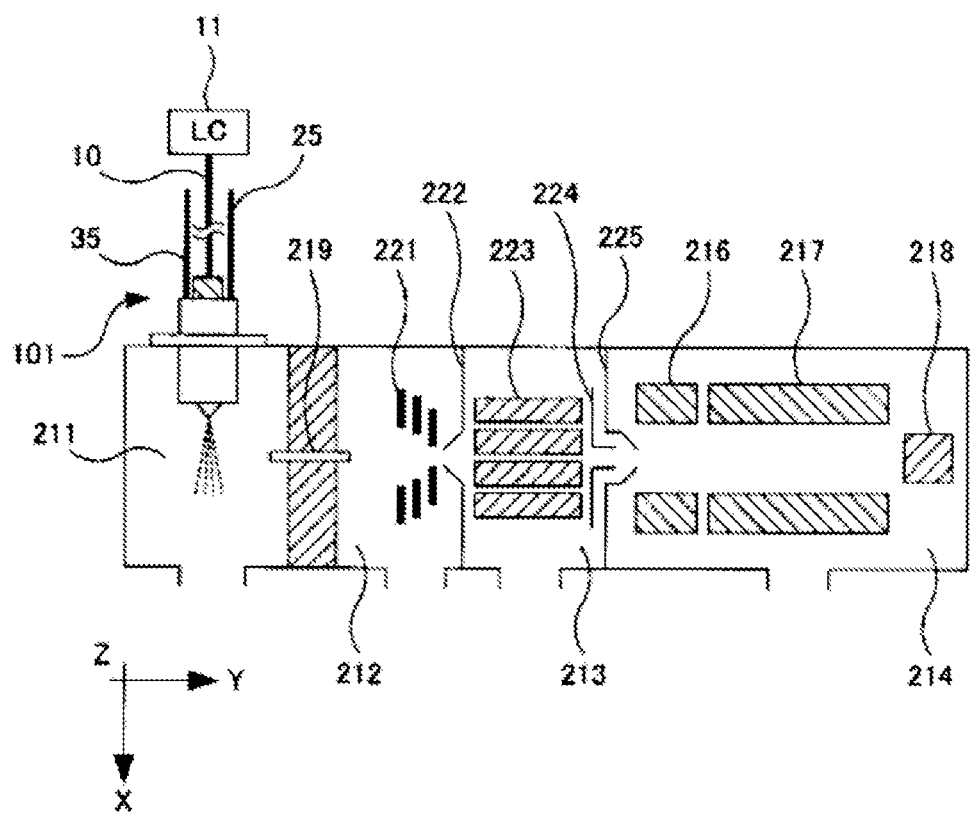
FIG. 3 is a simplified diagram illustrating an example of a liquid chromatography/mass spectrometry device based on ESI.

FIG. 1 is a simplified diagram illustrating an example of a liquid chromatography/mass spectrometry device using ESI according to the present invention, and FIG. 2 is a cross-sectional view of the ESI probe used in FIG. 1. It should be noted that elements which are the same as in the conventional liquid chromatography/mass spectrometry device described above will be assigned the same reference symbols.

In the liquid chromatography/mass spectrometry device, an ionization chamber 211, a first intermediate chamber 212 adjacent to the ionization chamber 211, a second intermediate chamber 213 adjacent to the first intermediate chamber 212, and an MS unit 214 adjacent to the second intermediate chamber 213 are disposed contiguously across intervening partition walls.

ESI probe 1 comprises a round tubular liquid sample channel 10 through which a liquid sample flows in the X direction, a round annular nebulizer gas channel 20 through which nebulizer gas flows in the X direction, a round annular heating gas channel 30 through which assist gas after heating (to about 500° C.) flows in the X direction, a heater 40 arranged in the heating gas channel 30, and an assist gas channel 33 through which assist gas before heating (at ambient temperature) flows in the −X direction.

The assist gas channel 33 comprises a main channel 33a formed at the outer circumference of the nebulizer gas channel 20 so as to have a round annular outer circumference and be coaxial with the nebulizer gas channel 20; a round tubular inlet channel 33b for introducing assist gas into the main channel 33a; and a round tubular connection channel 33c for introducing assist gas into the heating gas channel 30.

The main channel 33a is formed at the outer circumference of the nebulizer gas channel 20 so as to have a round annular outer circumference and be coaxial with the nebulizer gas channel 20, the inlet channel 33b is inserted from a portion of the top end surface of the main channel 33a to the bottom end of the main channel 33a, and another portion of the top end surface of the main channel 33a is connected to one end of the connection channel 33c. Furthermore, the other end of the inverted U-shaped connection channel 33c is connected to the top end of the heating channel 30b of the heating gas channel 30.

With this sort of assist gas channel 33, the assist gas introduced into the inlet channel 33b passes through the inlet channel 33b in the X direction and is then introduced from the bottom end of the inlet channel 33b into the bottom end of the main channel 33a. The assist gas which has been introduced into the bottom end of the main channel 33a flows over the entire circumference of the main channel 33a in the X direction and is then introduced into one end of the connection channel 33c. The assist gas which has been introduced into one end of the connection channel 33c flows through the connection channel 33c and is then introduced into the heating gas channel 30.

The heating gas channel 30 comprises a round annular channel 30a formed around the bottom end of the main channel 33a so as to have a round annular shape and be coaxial with the main channel 33a; and a round tubular heating channel 30b which is connected to a portion of the top end of the round annular channel 30a. The other end of the connection channel 33c is connected to the top end of the heating channel 30b, a heater 40 is arranged in the middle inside the heating channel 30b, and the bottom end of the heating channel 30b is connected to a portion of the top end of the round annular channel 30a. Furthermore, a heating gas outlet nozzle 32 is formed with an annular outer circumference coaxial with the main channel 33a around the bottom end of the main channel 33a on the bottom end of the round annular channel 30a. Namely, the main channel 33a is formed between the outside of the nebulizer gas channel 20 and the inside of the heating gas channel 30. Thus, the heat of the heater 40 and the heat of the heated assist gas are not transferred to the liquid sample channel 10, and furthermore the nebulizer gas channel 20 can be cooled by ambient temperature assist gas, and consequently the distance between the outside of the nebulizer gas channel 20 and the inside of the heating gas channel 30 can be made for instance 3 mm.

With the ESI probe 1 of the present invention, as described above, the thermal insulation effect between the outside of the nebulizer gas channel 20 and the inside of the heating gas channel 30 increases, the need to provide a space to create a predetermined minimum distance between the outside of the nebulizer gas channel 20 and the inside of the heating gas channel 30 is eliminated, and the size of the ESI probe 1 can be reduced. Furthermore, materials of relatively low heat resistance can be used as the electrical insulators 23 and 24, allowing costs to be reduced.

The ESI probe 1 described above had a configuration wherein the main channel 33a was formed at the outer circumference of the nebulizer gas channel 20 so as to have a round annual outer circumference and be coaxial with the nebulizer channel 20, but a configuration wherein the main channel 33a is formed only in places touched by the user or places where temperature increase is a problem is also possible.

The present invention can be used in ESI probes which ionize liquid samples eluted from a liquid chromatography unit, etc.

DESCRIPTION OF REFERENCES

1: ESI probe
10: Liquid sample channel
20: Nebulizer gas channel
22: Nebulizer gas outlet
30: Heating gas channel
32: Heating gas injection port
33: Assist gas channel
40: Heater (heating element)

What is claimed is:

1. A probe comprising:
   a tubular liquid sample channel through which a liquid sample flows in a specified direction;
   a nebulizer gas channel through which a nebulizer gas flows in the specified direction, formed at the outer circumference of said liquid sample channel so as to have a round annular outer circumference and be coaxial with the liquid sample channel;
   a heating gas channel for injecting an assist gas in the specified direction, wherein a heating gas injection port is formed around the outlet end of said nebulizer gas channel so as to have a round annular outer circumference and be coaxial to the nebulizer gas channel; and
   a heating element which is arranged inside said heating gas channel and heats the assist gas for injecting through said heating gas injection port,
   an assist gas channel formed in all or part of the space between said nebulizer gas channel and heating gas channel,
   wherein an inlet channel connects to a main channel of said assist gas channel at a first point of said main channel and another portion of the main channel connects to said heating gas channel at a second point disposed further from said heating gas injection port than said first point with respect to the specified direction thereby causing the assist gas, prior to being heated by said heating element, to flow through the assist gas channel, and the assist gas after being heated by said heating element to flow through the heating gas channel.

2. A probe as set forth in claim 1, characterized in that said assist gas channel is formed at the outer circumference of said nebulizer gas channel so as to have a round annular outer circumference and be coaxial with the nebulizer channel, and the assist gas prior to being heated by said heating element flows in a direction opposite to the specified direction, or in the specified direction.

3. A probe as set forth in claim 1, characterized in that said liquid sample channel is fabricated from metal, and a high voltage is applied to the outlet end of said liquid sample channel.

4. A probe as set forth in claim 2, characterized in that said liquid sample channel is fabricated from metal, and a high voltage is applied to the outlet end of said liquid sample channel.

* * * * *